(12) United States Patent
Polo

(10) Patent No.: US 11,525,109 B2
(45) Date of Patent: Dec. 13, 2022

(54) **STRAIN OF YEAST *SACCHAROMYCES BAYANUS* SUBSP. *UVARUM* DBVPG36P, ITS USE IN THE FERMENTATIVE PRODUCTION OF FOODS AND A METHOD FOR THE SELECTION OF THE STRAIN**

(71) Applicant: BIOENOLOGIA 2.0 S.R.L., Oderzo (IT)

(72) Inventor: Maurizio Polo, Fontanelle (IT)

(73) Assignee: Bioenologia 2.0 S.R.L., Oderzo (IT)

( * ) Notice: Subject to any disclaimer, the term of this patent is extended or adjusted under 35 U.S.C. 154(b) by 705 days.

(21) Appl. No.: 16/340,660

(22) PCT Filed: May 11, 2018

(86) PCT No.: PCT/IB2018/053290
§ 371 (c)(1),
(2) Date: Apr. 9, 2019

(87) PCT Pub. No.: WO2018/207141
PCT Pub. Date: Nov. 15, 2018

(65) Prior Publication Data
US 2020/0048592 A1 Feb. 13, 2020

(30) Foreign Application Priority Data
May 11, 2017 (IT) .................. 102017000051113

(51) Int. Cl.
| | |
|---|---|
| *C12G 1/02* | (2006.01) |
| *C12G 1/022* | (2006.01) |
| *A23L 33/14* | (2016.01) |
| *C12N 1/18* | (2006.01) |
| *C12R 1/85* | (2006.01) |

(52) U.S. Cl.
CPC ............ *C12G 1/0203* (2013.01); *A23L 33/14* (2016.08); *C12N 1/185* (2021.05); *C12G 2200/05* (2013.01); *C12R 2001/85* (2021.05)

(58) Field of Classification Search
CPC ... C12G 1/0203; C12G 2200/05; A23L 33/14; C12N 1/185; C12R 2001/85
USPC .......................................................... 426/15
See application file for complete search history.

(56) References Cited

U.S. PATENT DOCUMENTS

2010/0040732 A1* 2/2010 Van Drunen ........ A23C 11/106
426/18

FOREIGN PATENT DOCUMENTS

| EP | 1 978 083 A2 | 10/2008 | |
|---|---|---|---|
| EP | 1978083 A2 * | 10/2008 | ............... C12N 1/16 |
| EP | 2 277 990 A1 | 1/2011 | |
| EP | 2 634 247 A1 | 9/2013 | |

OTHER PUBLICATIONS

Dubourdieu, D. et al. (Am. J. Enol. Vitic. 57:81-88 (2006). Abstract. (Year: 2006).*
Tosi, E. et al. J. Appl. Microbiol. 107: 210-218 (Year: 2009).*
International Search Report and Written Opinion dated Jul. 16, 2019, issued in PCT Application No. PCT/IB2018/053290, filed May 11, 2018.
Etjen Bizaj et al., *A Breeding Strategy to Harness Flavor Diversity of Saccharomyces Interspecific Hybirds and Minimize Hydrogen Sulfide Production*, FEMS Yeast Research, vol. 12, No. 4, Jun. 1, 2012, pp. 456-465, XP055443493.
Mariana Tristezza et al., *Autochthonous Fermentation Starters for the Industrial Production of Negroamaro Wines*, Journal of Industrial Microbiology & Biotechnology; Official Journal of the Society for Industrial Microbiology, vol. 39, No. 1, Jun. 21, 2011, pp. 81-92, XP019996857.
Alexandra Verspohl et al., *Exploration of Genetic and Phenotypic Diversity within Saccharomyces uvarum for Driving Strain Improvement in Winemaking*, Applied Microbiology and Biotechnology, vol. 101, No. 6, Dec. 8, 2016, pp. 2507-2521, XP036164221.

* cited by examiner

*Primary Examiner* — Hamid R Badr
(74) *Attorney, Agent, or Firm* — Workman Nydegger

(57) ABSTRACT

The invention concerns a strain of *Saccharomyces bayanus* subsp. *uvarum* identified as SERIUS and deposited at the DBVPG with deposit number 36P. The invention further concerns the use of the strain of *Saccharomyces bayanus* subsp. *uvarum* identified as SERIUS (DBVPG 36P) as a food inoculate in the production of foods obtained through alcoholic fermentation, and a selection method for yeast strains of the group *Saccharomyces* adapted to alcoholic fermentation, particularly of grape, consisting of an isolation step for such yeasts from flowers.

11 Claims, 2 Drawing Sheets

STRAIN OF YEAST *SACCHAROMYCES BAYANUS* SUBSP. *UVARUM* DBVPG36P, ITS USE IN THE FERMENTATIVE PRODUCTION OF FOODS AND A METHOD FOR THE SELECTION OF THE STRAIN

FIELD OF THE ART

The present invention concerns a strain of yeast belonging to the species *Saccharomyces bayanus* subsp. *uvarum*, and a selection method for yeasts for oenological use from flowers. Furthermore, the invention refers to the use of the yeast strain in the fermentative production of foods.

State of the Art

The use of starter yeast cultures in wine production is a fundamental practice allowing the control and steering of the fermentative process.

The term selected yeast or selected starter is used to mean a yeast strain characterised by physiological, biochemical and oenological properties that are optimised with regard to the technological demands of the fermentation processes in terms of purity (Pretorius, 2000).

The use of selected yeasts ensures the prompt initiation of fermentation since the quality and quantity of yeast added to the must are carefully selected; it allows greater control of the fermentative process by the operator opting to conduct fermentation without said process being left to yeasts naturally present in grapes that do not always have positive characteristics; it reduces the problems of arrest or slowing-down of the process, typical of spontaneous fermentation processes; it achieves good sugar transformation yields into alcohol, reducing the possibility of other microorganisms becoming established in the wine, thus damaging it (for example acetic bacteria); it reduces or eliminates anomalous organoleptic characteristics and, by no means last, it contributes towards the standardisation of production of a given wine, thus allowing it to be recognisable by the consumer year after year (Fleet and Heard, 1993).

Predominantly, the yeast selection occurs by means of the isolation of yeast strains from must or grapes, that are subjected to fermentation and oenological characterisation testing. Said tests are very laborious and require a great deal of time, in that they envisage the study of numerous physiological and metabolic characteristics for the yeast. In addition, musts and grapes can contain multiple copies of the same strain, whereby there is a risk of isolating said multiple copies and thus conducting duplicate tests.

The important oenological characteristics can be subdivided into two groups: those with technological importance, influencing the progression of the vinification process, and those affecting quality, influencing the chemical and sensory characteristics of the wines (Zambonelli, 2003). The term technological characteristics is understood to mean the characteristics associated with the fermentation activity of the yeasts (absolute alcoholigenic power, fermentative force, fermentation initiation rate), while the quality characteristics include those characteristics contributing towards the aroma, and more generally, to the organoleptic quality of the wine, such as for example the production of glycerol, volatile substances and sulphurated compounds (Pretorius, 2000; Fleet, 2008).

The major technological characteristics include the fermentative or alcoholigenic power, which, according to Delfini, is the maximum alcohol level (understood as % ethanol) produced by a given yeast by means of the fermentation of a must containing excess sugar (Delfini, 1995). The main ethyl alcohol produced by the activity of yeasts under anoxic conditions is the compound exercising an inhibitory action on all microorganisms. Since, for oenological use, yeasts require significant performance characteristics, for example, for the production of wines with high alcohol content, also the resistance (alcohol tolerance) to ethyl alcohol has, evidently, a fundamental importance.

An additional important technological characteristic is the fermentative force (or rate of fermentation), expressing the rate at which the yeast initiates fermentation, even in the presence of antiseptics at legally permitted doses and at temperatures between 15° C. and 30° C. Rapid initiation of the fermentative process is one of the characteristics an oenological yeast must possess regardless of its type of use (fresh or dried) and therefore must be considered a fundamental requirement in the selection of yeasts for vinification.

An additional, very important characteristic is resistance to sulphur dioxide $SO_2$, i.e. the ability to maintain unaltered or sufficiently high the fermentation rate in the presence of selective doses of $SO_2$ added to musts in order to avoid oxidation and achieve a suitable microbiological stability. Where $SO_2$ supplemented wines are produced, it is therefore important to have strains available that are resistant to this antiseptic, in order to avoid initiation problems affecting the fermentation process.

Another important aspect concerns the methods of growth, i.e. the behaviour of the yeast cells on completion of the budding process, since said characteristic can affect management of the fermentation process. Yeast growth may be distinguished between pulverulent, flocculent or aggregate growth. The sedimentation rate of the strain is thus an additional positive characteristic, since it aids wine clarification and filtration operations.

The strains that cloud wine in the most annoying and persistent manner are the foam generating strains. Foam generating capacity is a strain-dependent characteristic, associated with the hydrophobicity of the cell wall. In many strains (20-30%) the cells adhere to the $CO_2$ bubbles produced during fermentation, and these bubbles, upon arrival at the surface, rather than breaking up, fuse together and increase in volume, giving rise to foams which take on a grey-brown colour due to the presence of the cells. The absence or reduced production of foam is a positive characteristic, both in primary fermentations and in refermentations, since it reduces the volume occupied by the must.

With regard to the qualitative characteristics, to be subsequently described in detail, the main considerations include:

low or zero production of hydrogen sulphide;
 the production or degradation of malic acid (as a function of the must and the oenological vintage);
 high glycerol production;
 low acetic acid production;
 high aromatic potential.

From the qualitative viewpoint, the sulphurated compounds mainly consist of hydrogen sulphide (or $H_2S$) and sulphur dioxide ($SO_2$); said compounds are always produced by the *S. cerevisiae* strains commercially available as wine starters, even though in different and variable quantities depending on the strain.

Vinification using non-producing or low $H_2S$ producing yeasts is particularly advantageous for those varieties that are peculiarly predisposed to "reduction". Indeed, hydrogen sulphide is the main compound of light mercaptans, and has the drawback of having the smell of rotten eggs. Wines displaying olfactive defects traced to the presence of $H_2S$ have concentrations of the latter varying between 0.8 and 80 µg/l (Suzzi and Tofalo, 2014). $H_2S$ can also react with other compounds present in wine, altering the aromatic profile. This is mainly produced during alcoholic fermentation, as a result of yeast action.

Hence, use of a yeast that does not produce, or produces little hydrogen sulphide, not only allows cleaner fermentations and more fragrant wines, but also delays and/or avoids racking on completion of fermentation, allowing the wine to remain longer on the lees, with consequent enrichment of mannoproteins and other substances resulting from yeast lysis. It is known that $H_2S$ production in *Saccharomyces cerevisiae* ranges from 0 µg/litre to 300 µg/litre and that the quantity produced is a strain-dependent characteristic. Furthermore, data from the literature shows that only about 1% of oenological strains is incapable of producing $H_2S$ (Zambonelli et al., 1984).

Also, $SO_2$ production by yeasts shows broad variability. Certain strains that produce significant quantities of $SO_2$ (100-120 mg/l) also have a tendency to produce significant quantities of acetaldehyde (to defend against said antiseptic) and the result, on completion of fermentation, is a high concentration of bound $SO_2$, which can compromise wine quality. Hence, during oenological starter strain selection operations, preference should be given to strains that produce low levels of $SO_2$ (maximum of 10-20 mg/l) (Vincenzini et al., 2005).

With regard to the production of malic acid during alcoholic fermentation, this represents an advantage in the majority of vinification processes involving quality white grapes, in that the presence of high quantities of malic acid gives an increased sensation of freshness to the resulting wine, in particular an acid sensation, considered more intense, in comparison to tartaric acid.

An additional advantage is that the production of malic acid allows lower pH, with resulting increased sulphur dioxide activity and, in general, increased microbiological stability in addition to increased overall acidity. Said production by yeasts of oenological interest has been described in the known art for certain cryotolerant yeasts, capable of producing up to 1 g/l of malic acid during the fermentation process (Castellari et al., 1994).

Another secondary product of fermentation by yeasts is glycerol.

After ethanol and $CO_2$, glycerol is the compound produced in greatest quantities during alcoholic fermentation. This significantly influences the "body" of the wine, contributing towards giving the wines the characteristics of "fullness" and "sweetness", with a perception threshold corresponding to about 5.2 g/l. The concentration of glycerol present in the wine depends on the concentration of sugars present in the must, the fermentation conditions and the strain of yeast.

In particular, in vinification processes, *Saccharomyces* can produce from 2 to 10 g/l, depending on the yeast species and strain. Generally, *S. cerevisiae* is the yeast producing the lowest quantities of glycerol, and this is the main reason for its high ethanol yield. In reality, this compound is not a secondary fermentation product since it is derived directly from the sugars, and, strain for strain, the quantity produced is proportional to their concentration (Zambonelli et al., 2000).

Among the secondary products, even though negative, a very important role is played by acetic acid, which, during fermentation, is derived from degradation of the sugars due to the oxidation of acetaldehyde (Ribéreau-Gayon, 2000).

Besides the species, the ability to produce greater or reduced quantities of acetic acid is a characteristic that varies as a function of the strain.

Said ability to produce acetic acid is actually defined by the term fermentative purity, and is expressed as the ratio between volatile acidity formed and ethyl alcohol produced. The best strains are those that have the lowest fermentative purity value and, generally, the yeasts used for oenological ends should not produce quantities of acetic acid higher than 0.4 g/l.

However, the volatile acidity of wines can be the result of several origins, and is not only the result of yeast activity. Indeed, the final concentration of acetic acid in wine also depends on the quality of the grapes and the vinification conditions. Acetaldehyde is the most important carbonyl compound formed during fermentation, and represents over 90% of the total wine aldehyde content. It is a normal product of alcoholic fermentation, and its content in wine can vary significantly (10-300 mg/l) depending on the yeast strain and also the vinification conditions, and the concentration of sulphur dioxide, to which the acetaldehyde is bound. Evaluation of the acetaldehyde content is used as an indicator of the degree of oxidation of the wine. A low concentration of said compound in wine gives the latter a pleasant fruity aroma; however, at increasing concentrations, it gives rise to a pungent and oxidised odour and a herb-like flavour, so as to make the wine no longer marketable when the acetaldehyde concentration exceeds 500 mg/l.

For white wines, the mean value is generally 80 mg/l. It is known that one of the main factors determining acetaldehyde content variability is the strain of yeast. It is likewise also known that sulphur dioxide can induce the production of acetaldehyde by yeasts due to the correlation between the resistance of the yeasts themselves to sulphur dioxide.

The higher alcohols, generally represented in wine by n-propanol, isobutanol, amyl alcohol and 2-phenyl ethyl alcohol, are secondary yeast fermentation products, and are compounds that can significantly influence the aroma of wine. Said compounds are predominantly derived from metabolism of the aminoacids present in the must, but also from the metabolism of glucose without the involvement of precursor aminoacids. Indeed, there is no direct correlation between the quantities of aminoacids present in the must and the higher alcohols present in the wine. The production of said compounds is mainly due to the action of the yeast strains that can produce from 100 to 500 mg/l, depending on the composition of the medium, the availability of oxygen, the source of nitrogen and the initial sugar concentration. Generally, when their total concentration is below 300 mg/l, they lend a positive contribution to the complexity of the aroma, while when present in concentrations higher than 400 mg/l, they lend a negative quality to the product (Suzzi and Tofalo, 2014). The exception is 2-phenylethanol, which releases a rose-scented fragrance, and even at high concentrations contributes positively to the aroma of the wine (Vincenzini, 2005).

During fermentation, yeasts can produce esters resulting from the condensation of acetic acid and fatty acids, predominantly medium chain, with ethanol or other alcohols present in the wine, and themselves also produced by yeast metabolism. Yeast esterase activity is very important in the vinification process since it has a powerful effect on the sensory characteristics of the wine, producing the majority and most important of the fermentation aromas. The influence of esters on wine quality can be negative and unwelcome, particularly in the case of ethyl acetate, which confers the typical vinegar (or even solvent) scent. On the other hand, the production of isoamyl acetate or isobutyl acetate is positive, as it is responsible for a fruity character.

DESCRIPTION OF THE INVENTION

The scope of the invention is to provide a strain of yeast from the species *Saccharomyces bayanus* subsp. *uvarum*, equipped with the technological and oenological characteristics allowing good fermentation of the must, allowing the production of a pleasing wine with increased and balanced aromatic complexity.

An additional scope is to provide a strain that produces malic acid and glycerol in high quantities and, at the same time, does not produce hydrogen sulphide during alcoholic fermentation.

A further scope of the present invention is to identify a strain of yeast suitable for use as a parent strain for obtaining yeast hybrids with oenological potential. The provision of a yeast autolysate to be used as a fermentation activator is also a scope of the present invention.

By no means the final scope of the invention is the optimization of a perfected and rapid method for the selection of yeast strains for oenological use, particularly yeasts from the species *Saccharomyces cerevisiae* and *bayanus* isolated from flowers.

The aforementioned scopes are achieved by means of the strain of yeast as characterised in claim 1, and precisely by a strain of *Saccharomyces bayanus* subsp. *uvarum* identified as SERIUS, and deposited at the DBVPG with deposit number 36P, and by the selection method for yeast strains for oenological use, the characteristics of which are set out subsequently, and precisely, by a selection method for yeast strains of the species *Saccharomyces cerevisiae*, *Saccharomyces bayanus* and *Saccharomyces bayanus* subsp. *uvarum*, adapted for alcoholic fermentation, particularly of grapes, isolated from flowers.

The yeast strain *Saccharomyces bayanus* subsp. *uvarum* according to the invention possesses optimal oenological characteristics, both technological and qualitative, and has been isolated from flowers in an area of the Veneto region with high grape-wine producing activity. The strain has been identified by the name SERIUS, and has been deposited in accordance with the Treaty of Budapest, on 24 May 2016 with the "Industrial Yeasts Collection" DBVPG in Perugia, with deposit number DBVPG36P.

The strain has also been selected for its essentially non-existent hydrogen sulphide production, a very rare characteristic in yeast strains of the genus *Saccharomyces*. Indeed, on plates of Biggy agar culture medium, preferably used to verify the ability to produce $H_2S$, the colonies are white, thus demonstrating the strain's inability to produce this metabolite.

Another positive aspect observed with this yeast concerns the production of glycerol. Indeed, in must, the strain produces glycerol in greater concentrations with respect to commercially available *S. cerevisiae* strains used as control.

Advantageously, the quantity of glycerol produced has been analysed in white berry grape musts and red berry grape musts and, with both types of grape, the quantity of glycerol naturally produced was greater with respect to the corresponding must obtained with the commercially available reference strain.

Advantageously, the wine produced using the strain according to the invention has a glycerol concentration naturally produced by the strain higher than about 8.5 g/l, preferably higher than about 9.5 g/l, more preferably higher than about 10 g/l.

By the term "produced by the strain" (herein and in similar contexts) it is understood that the compound has been produced as a result of fermentation using the strain, and has not been added artificially.

The strain according to the invention has also been selected for its unexpected ability to produce malic acid.

Advantageously, the strain of the invention has the ability to produce a wine with a quantity of malic acid higher than about 0.5 g/l, preferably higher than about 1 g/l, more preferably higher than about 2 g/l. This molecule is particularly advantageous in vinification processes, particularly for quality white grape processes, since it gives the wine an increased sensation of freshness.

An additional and advantageous aspect is given by the fact that a high quantity of malic acid makes it possible to have wine with lower pH, a characteristic allowing greater sulphur dioxide activity.

Still advantageously, the strain of the invention with its unexpectedly high malic acid production makes it possible to obtain increased microbiological stability for the wine, with increased total acidity.

Due to its technological qualities, the SERIUS strain is therefore markedly superior to the commercial strains currently available.

Advantageously, the strain has good fermentation capacity, with mean weight loss values analogous to those observed in commercial yeasts of the species *Saccharomyces cerevisiae* and with fermentation closure times that vary as a function of the type of must used and the fermentation temperature, with durations, at optimal fermentation temperature, of between 10 to 15 days.

Still advantageously, the strain of the invention has good fermentative capacity, even at low temperatures, particularly at temperatures between 12° C. and 15° C., thus also allowing its use for the fermentation of wines at low temperatures, and hence increasing the possibility of activating specific known biochemical reactions leading to the production of aromatic compounds, adapted to improving wine quality.

For the strain of the invention, the ability to produce acetic acid in natural white and red berry must has also been assessed, and the results obtained demonstrate that the strain SERIUS is characterised by the ability to maintain very low volatile acidity values; in particular, the values obtained are generally lower compared to the values obtained from comparative fermentations with commercially available *S. cerevisiae* strains.

The strain of the present invention has also been selected based on its so-called killer activity, namely, the ability to produce toxins that cause the death of other yeasts; indeed, in the case where mixtures of strains are used, the strains to be used must necessarily be compatible with one another, namely, incapable of producing the killer toxins that can inhibit the other strains present in the mixture. From the analysis performed, it was advantageously shown that the strain SERIUS is not capable of inhibiting other yeasts and, even more advantageously, the strain has not in turn been inhibited by any of the yeasts tested.

The strain has been taxonomically classified at the species level by means of sequencing of the ITS (Internal Transcribed Spacer) region of the ribosomal operon, and subsequent compared by means of alignment with the homologous region available for the phylogenetically more related species of the genus *Saccharomyces* Meyen ex Rees (1870), in accordance with Vaughan-*Martini* & *Martini*; said molecular analysis has allowed identification of the strain SERIUS as *Saccharomyces bayanus* subsp. *uvarum*.

The strain has also been subjected to genotypic characterisation by means of analysis of the mitochondrial DNA restriction profiles using the enzyme Hinf I, as described by Zilio et al. and reported in detail in example 1, point 1.6 and, further, by means of the use of particular molecular markers, known as microsatellites, in accordance with a method, also described in detail in example 1, point 1.6.

If transferred to suitable culture medium under limiting nutrient conditions, the strain according to the invention is capable of sporulation. Improved conditions for inducing sporulation of the strain SERIUS are obtained in SP medium (1% potassium acetate; 0.1% yeast extract; 0.05% glucose; 1.8% agar) incubated at 25° C. for 7-10 days.

Other positive aspects found for this yeast have been observed during growth in synthetic and natural must (example 2).

The yeast forming the subject of this patent has the oenological characteristics reported below: sugars consumed after 2 days (fermentative vigour): about 4-5 g/100 ml; sugars consumed after 7 days: about 15-17 g/100 ml; 10-15 days: duration of fermentation at optimal temperature; low foam production.

A particularly advantageous positive aspect observed with this yeast concerns the production of $H_2S$, which is substantially absent.

Furthermore, the strain is resistant to an $SO_2$ concentration of at least 50, preferably 100, even more preferably 200 and ulteriorly preferably 300 ppm.

The strain also has high resistance to copper, in particular it is resistant to a copper concentration of 300 μmol/l. Advantageously, said copper concentration has also been shown to be superior to the copper resistance of commercially available yeast strains, equal to about 50-100 μmol/l. Preferably, the strain is stored in frozen form (−80° C.) in the presence of appropriate cryoprotective agents (40% w/w glycerol) or preserved by means of lyophilisation/desiccation. Freezing or lyophilisation/desiccation are achieved using methods known to those skilled in the art.

The strain according to the invention may be advantageously industrialised in a cream form, desiccated form, lyophilized form, or in the form of a paste, depending on the requirements of the user.

The strain according to the invention is adapted to being used as a food inoculum in the production of foods, obtained through alcoholic fermentation. Foods that are producible with this yeast include for example bread, milk-based products, cider, bear, spumante and wine. Other alcoholic beverages obtained from the alcoholic fermentation of other fruits or cereals, such as wheat or rice, are also however conceivable. The strain is also adapted to being used as a probiotic in dietary supplements or in foods. Preliminary characterisation tests suggest this strain is resistant to acidity and bile salts, and therefore has the possibility of surviving gastric transit.

Advantageously, the strain *S. bayanus* subsp. *uvarum* SERIUS of the invention has been particularly suitable for the production of a yeast autolysate to be used as a fermentation activator in the production of wine and other alcoholic beverages.

According to one preferred executive variant of the invention, the strain is used as an inoculum in vinification in order to obtain wines, for example red wines, rosé wines or white wines. In addition, it can also be used in both primary fermentation and in refermentation.

Advantageously, use of the strain of the invention in a vinification process allows the production of a wine with pleasing and balanced aromas, with a substantially non-existent $H_2S$ concentration, high glycerol concentration and high malic acid concentration.

Advantageously, the wine is a wine produced from grapes selected from white berry grapes and red berry grapes. In addition, said grapes may be derived from both native vine varieties and from international vine varieties.

In particular, vinification tests performed on grapes selected from garganega, kerner, trebbiano, merlot, nerello mascalese, nero d'avola and traminer have made it possible to obtain wines with pleasing aroma and balanced flavour.

According to the preferred embodiment of the invention, the strain SERIUS is used for the production of wine containing glycerol and malic acid, produced naturally by the strain in the following concentrations: glycerol higher than about 8.5 g/l, preferably higher than about 9.5 g/l, more preferably higher than about 10 g/l; malic acid higher than about 0.5 g/l, preferably higher than about 1 g/l, more preferably higher than about 2 g/l. The strain SERIUS can be easily cultivated and is therefore particularly suited to being used to produce biomass, even on an industrial scale, using known standard methods.

Preferably, biomass production using the strain SERIUS occurs on a synthetic medium containing dextrose, yeast extract, vitamins and mineral salts, with batch-type fermentation (first 24 hours) followed by fed-batch type fermentation for a further 20-24 hours. Still preferably, growth occurs at a temperature of between 29 and 31° C. The strain produces ethanol and is therefore particularly applicable in food fermentation. The strain is not pathogenic for humans or animals.

Another aspect of the invention concerns a food inoculum consisting of the strain of *Saccharomyces bayanus* identified as SERIUS (DBVPG 36P). Preferably, the food inoculum is a wine starter.

An additional aspect of the invention concerns a wine obtainable by means of use according to the invention. Advantageously, the wine is a wine obtained from the fermentation of grapes selected from white berry grapes and red berry grapes. Advantageously, said grapes may come from both native vine varieties and from international vine varieties.

Cultures of the yeast *Saccharomyces bayanus* subsp. *uvarum* SERIUS, obtainable by means of the reproduction and/or multiplication of the strain SERIUS of the present invention, capable of being used as food inoculates in the production of foods obtained through alcoholic fermentation, are also to be understood as being protected by the present invention. According to the preferred executive variant of the present invention, said strains are adapted to being used in alcoholic fermentation processes for the production of wine, i.e. in vinification processes.

Particularly preferred are cultures obtainable from the reproduction or multiplication of the strain SERIUS of the invention, adapted to being used for the production of wine produced from grapes selected from white berry grapes and red berry grapes, wherein said grapes may come from both native vine varieties and from international vine varieties.

Preferably, said cultures are adapted to being used for the production of a wine containing glycerol and malic acid, produced naturally by the strains in the following concentrations: glycerol higher than about 8.5 g/l, preferably higher than about 9.5 g/l, more preferably higher than about 10 g/l; malic acid higher than about 0.5 g/l, preferably higher than about 1 g/l, more preferably higher than about 2 g/l.

Independently of their species, it is known that yeasts can reproduce sexually in order to ensure the survival of the species, creating genetic diversity, and hybridisation is an essential part of this sexual reproduction cycle, which can exist in nature as it is or be induced in the laboratory. The aforementioned hybridisation allows the attainment of novel yeast hybrids originating from a parental strain, according to a process that is absolutely non-GMO. Consequently, the establishment of hybrid strains is a mode of evolution for natural yeasts.

Hence, the yeast strains obtained through hybridisation of the strain SERIUS with a yeast strain belonging to the same species, or rather a *Saccharomyces* strain, by means of a so-called intraspecies hybridisation, also form a part of the present invention.

However, it is not excluded that according to executive variants of the invention, strains may be obtained by hybridisation of the strain SERIUS with yeast strains from other species, by means of interspecies hybridisation.

Another aspect of the invention concerns a selection method for yeast strains from flowers, particularly *Saccharomyces cerevisiae, Saccharomyces bayanus* and *Saccharomyces bayanus* subsp. *uvarum* strains, adapted to alcoholic fermentation, particularly of grapes. Obviously, sampling from flowers may be also transferred to other strain isolation matrices (for example fruit, medicinal herbs).

The selection method according to the present invention preferably consists of a step for yeast isolation from flowers, preferably a yeast identification step, a seeding phase for the isolated yeasts on plates, in order to identify strains that are non-producers or low producers of $H_2S$, and an inoculation phase in must and the vinification of grapes with the purpose of studying their technological and quality characteristics.

Preferably, the grapes used are grapes selected from white berry grapes or red berry grapes.

According to the preferred embodiment of the method of the invention, the wine obtained during the aforementioned vinification step is analysed and the concentrations of glycerol and malic acid present therein are determined. A sensory evaluation is also performed with the aim of identifying unpleasant odours traceable to the presence of sulphurated compounds. Particular attention is paid to the identification of reduction defects due to the presence of $H_2S$. Subsequently, strains are selected with enhanced fermentative vigour, producing wines where the concentrations of glycerol and malic acid meet the following limits: glycerol higher than about 8.5 g/l, preferably higher than about 9.5 g/l, more preferably higher than about 10 g/l; malic acid higher than about 0.5 g/l, preferably higher than about 1 g/l, more preferably higher than about 2 g/l; furthermore, sensory examination must give no olfactory perception of reduction defects due to the presence of $H_2S$, i.e. preferably less than 1-1.5 g/l.

Advantageously, the analysis of this specific combination of compounds has been shown to be very suitable for the replacement of further and laborious characterisation processes, and the finding of strains producing wines with pleasing and balanced aroma.

In one preferred variant of the invention, the selection method for yeast strains from the species *Saccharomyces* previously specified as adapted to alcoholic fermentation, particularly of grapes, consists of the following steps:

a) sampling of flowers, preferably in spring and in areas of high grape-wine producing activity, and even more preferably away from wineries, in order to avoid contamination with commercial yeasts used in wineries that may be present not just in the wineries, but also in the adjoining areas;

b) fermentation of the samples on suitable substrates and cultivation of the fermented samples on isolation media, preferably containing bromocresol green;

c) if the isolation medium contains bromocresol green, the identification of presumed yeast strains of the genus *Saccharomyces* based on colony morphology and colour, and their discrimination from non-*Saccharomyces* yeasts of lesser oenological interest;

d) identification of isolates belonging to the genus *Saccharomyces* by means of genetic analysis of the yeast colonies isolated in step b) or step c); advantageously, said genetic analysis, performed using molecular methods, allows both identification of the species of origin and identification of the various strains, or rather individuals, present within a given species;

e) laboratory fermentation of the strains selected in step d) on synthetic must and/or on natural must, and subsequent selection of the strains with the most interesting technological and oenological characteristics, and at the same time seeding the strains in Biggy agar medium in order to identify those that are non-producers or low producers of $H_2S$;

f) the winery vinification of the strains selected in step e) and selection of the most suitable strains based on the results obtained through chemical analysis of the wine obtained, preferably including pH, residual sugars, alcohol, total acidity, volatile acidity parameters, and, in particular, the quantity of glycerol, malic acid and preferably hydrogen sulphide, where the latter is assessed by olfactory means.

Preferably the collection of flowers and their subsequent processing is performed by avoiding touching the flowers with the hands and with a periodic sterilisation of the sampling equipment, for steps a) and b), with the aim of limiting contamination as much as possible.

By way of non-limiting example, on arrival in the laboratory, the flowers are transferred into sterile flasks containing 200 ml of synthetic must or other culture medium capable of sustaining the growth of any yeasts present. The addition of an antibiotic to each sample, in order to avoid the proliferation of any bacteria, has been shown to be particularly useful.

Advantageously, the preparations are overlaid with sterile paraffin oil in order to avoid the growth of surface mould.

Samples with obvious fermentation underway are processed for isolation of the yeasts in the subsequent step b) or c). A very suitable and preferred isolation medium for said step is WL agar isolation medium (4.0 g/l yeast extract, 5.0 g/l tryptone, 50 g/l glucose, 550 mg/l potassium phosphate monobasic, 425 mg/l potassium chloride, 125 mg/l calcium chloride, 125 mg/l magnesium sulphate, 2.5 mg/l ferrous chloride, 2.5 mg/l manganese sulphate, 22 mg/l bromocresol green, 20 g/l agar, final pH 5.5±2). The salient characteristic of this medium is that it contains a dye, bromocresol green, which is capable of being absorbed by yeasts to a varying extent. It is therefore possible to characterise the microorganism based on colony morphology and the colour it assumes. Strains belonging to the genus *Saccharomyces* absorb bromocresol green poorly, and therefore their colonies assume a colour that varies from cream to green, allowing their discrimination from any non-*Saccharomyces* yeasts.

Advantageously, the use of bromocresol green and the execution of step c) allows simple reduction, and in an initial step of the method, the number of strains to be subjected to the subsequent step d).

Still advantageously, according to one executive variant of the method of the invention, prior to step d), the colonies to be analysed are subjected to purification by means of one or more reseeding passes on suitable medium. Preferably, any reseeding occurs on WL agar growth medium. Advantageously, the procedure is repeated in order to guarantee that each isolate definitely originates from a single colony.

Step c) is already somewhat selective for the isolation of strains belonging to the group *Saccharomyces*, but in addition to *Saccharomyces* there are also other strains that, in this culture medium, may display morphology and colouring very similar to those of the *Saccharomyces* yeasts. Therefore, in order to eliminate these strains from the samples and give definitive identification to the isolates, it is preferable to perform step d) which, by means of a rapid and simple to execute genetic method, makes it possible to perform screening on a large number of isolates, thus eliminating yeasts not belonging to the genus *Saccharomyces* and identifying any strains (=individuals) that should be present within the framework of a given species.

Advantageously, said preliminary genetic evaluation reduces the risk of performing the technological characterisation on yeasts that are potentially not adapted to the production of wine and, equally advantageously, allows the exclusion of any multiple copies of the same strain that may be present in a given sample.

Still advantageously, said preliminary analysis avoids the need to technologically and chemically test strains not belonging to the genus *Saccharomyces*.

Further advantageously, said analysis makes it possible to perform the technological and oenological characterisation only on truly diverse strains, and not on any possible multiple copies of the same strain.

In order to confirm the origin of the genus *Saccharomyces* and hence exclude yeasts belonging to different genuses, and hence uninteresting from the oenological viewpoint, it is preferable to use genetic characterisation envisaging the use of PCR technique. Both specific PCR techniques, capable of recognising the various yeast species, and RAPD-PCR (Random Amplified Polymorphic DNA analysis) techniques, known to those skilled in the sector, may be used for this purpose.

Advantageously, in cases where the use of PCR methods does not allow reliable strain identification, it is possible to resort to potential analysis of the rDNA sequence; this analysis makes it possible to distinguish between *S. cerevisiae, S. bayanus* and *S. bayanus* subsp. *uvarum*, species that are phylogenetically closely related and with high oenological interest, with such metabolic characteristics as to allow them to survive and grow in wine. Preferably, sequencing concerns the ITS (Internal Transcribed Spacer) region of the ribosomal operon.

According to the preferred embodiment of the method of the invention, the genetic characterisation at strain level in step d) is performed by means of analysis of the mitochondrial DNA restriction profile, obtained by enzyme digestion of total DNA. Enzyme digestion of total DNA is preferably performed using the enzyme Hinf I. Genetic analysis of this type makes it possible to bring yeasts together into groups, each of which with a different genetic profile, common to all isolates belonging to that grouping. Based on the genetic data collected, it is then possible to perform screening on the yeasts collected, avoiding the selection of multiple copies of the same strain.

According to one executive variant of the method of the invention, genetic characterisation by means of restriction polymorphism analysis of mitochondrial DNA is used in association with microsatellite analysis. Microsatellites are repetitive sequences of non-coding DNA, consisting of very short repeat units (1-5 bp) arranged as tandem repeats that can be used as molecular markers of genetic loci. According to the preferred embodiment of the method of the invention, microsatellite analysis for the species *Saccharomyces bayanus* subsp. *uvarum* is performed on the eight most variable loci, described by Masneuf-Pomarede et al. in 2016. The analysis conditions are subsequently reported in detail (example 1, point 1.6). Generally, a reaction is performed for each locus named: SuYIL130W (16 allelic forms), SuYHR102W (8 allelic forms), SuYKR045C (10 allelic forms), SuHTZ1PLB3 (7 allelic forms), SuARS409 (5 allelic forms), SuYHR042-043 (5 allelic forms), SuYBR049C (5 allelic forms), SuYGC170W (4 allelic forms). Subsequently, for definition of the profile and characterisation of the strains, amplification of PCR products relating to the eight aforementioned loci is performed in addition to agarose gel electrophoresis migration, in accordance with known methods.

Advantageously, according to the method of the invention, subsequently to step d), optionally, for characterisation of the yeasts *S. bayanus* subsp. *uvarum*, a further analysis of the eight loci described above is performed by means of multiplex PCR, preferably two multiplex-PCR reactions, defined as multiplex PCR1 and multiplex PCR2. By means of said multiplex PCR, it is possible to simultaneously amplify more than a locus at a time. In particular, multiplex PCR1 and multiplex PCR2 allow the amplification of three and five loci respectively. In detail, multiplex PCR1 allows analysis of the DNA-microsatellite profile for the loci SuYIL130W, SuYHR102W and SuYGC170W, while multiplex-PCR2 makes it possible to obtain the DNA-microsatellite profile for the loci SuYKR045C, SuHTZ1PLB3, SuARS409, SuYHR042-043 and SuYBR049C.

Optionally, according to the preferred embodiment of the method of the invention, to further characterise the yeasts *S. bayanus* subsp. *uvarum*, prior to step e), it is possible to perform further genetic analysis by means of capillary electrophoresis based on amplification of the four loci characterised by a greater number of allelic forms, selected in accordance with data reported in the literature.

Advantageously, said characterisation makes it possible to define the exact size of the PCR products for the loci considered.

According to the present invention, the loci considered are the following: SuYIL130W, SuYHR102W, SuYKR045C and SuHTZ1PLB3.

Preferably, for the characterisation of step e) at the technological level, the following parameters are evaluated: fermentative vigour, understood to be the quantity of sugar consumed after 2 and after 7 days, and the duration of fermentation, the foam production capacity, type of growth, hydrogen sulphide production (on Biggy Agar medium), glycerol production, volatile acidity production, the ability to produce or degrade malic acid, the olfactory profile of the fermentates.

With regard to the progression of the fermentations, these are monitored on samples of synthetic must and/or natural must, preferably on both types of must. The main parameters monitored preferably concern: pH, residual sugars, alcohol level, total acidity, volatile acidity, fermentative vigour, glycerol production, production/degradation of malic acid, olfactory profile. The in-winery vinification tests for step f) are preferably performed on musts from white berry grapes and musts from red berry grapes.

Advantageously, analysis of fermentation progression for the strains on musts from both white berry and red berry makes it possible to check progression and evaluate the activity of a strain for the production of white, rosé and red wines, according to specific needs.

Particularly advantageously, the vinification phase of the method according to the invention is performed on grapes from both native vine varieties and international vine varieties. Preferably, the concentrations of glycerol, malic acid and hydrogen sulphide are determined in the wine obtained, and wine-producing strains are selected where the concentrations meet the following limits: glycerol higher than about 8.5 g/l, preferably higher than about 9.5 g/l, more preferably higher than about 10 g/l; malic acid higher than about 0.5 g/l, preferably higher than about 1 g/l, more preferably higher than about 2 g/l; and hydrogen sulphide below the olfactory perception level, i.e. less than about 1-1.5 µg/l. Advantageously, the wine produced using the strain SERIUS is characterised by the presence of high quantities of glycerol and malic acid, while the quantity of hydrogen sulphide is particularly reduced. In particular, the wine produced by the strain of the invention has glycerol in quantities exceeding 9 g/l, malic acid in quantities exceeding 1.1 g/l and $H_2S$ in quantities less than the olfactory level of perception.

The technological and chemical parameters examined can vary depending on the characteristics required for the strain and also depend on the type of wine to be produced using the strain selected. Selection of the most suitable strains at the end of the individual steps is preferably a combined selection considering all the results of all analyses performed.

This selection method guarantees the screening of multiple yeast isolates originating from flowers.

Particular examples of execution of the individual steps have been described in examples 1, 2 and 3. The individual steps should be considered as being independent from one another, i.e. the execution of step d) in a defined manner does not automatically imply, for example, the execution of step e) precisely as reported in the examples. The parameters within a step (e.g. the types of technological parameters under test) may be altered independently of the other steps.

Figure 1:
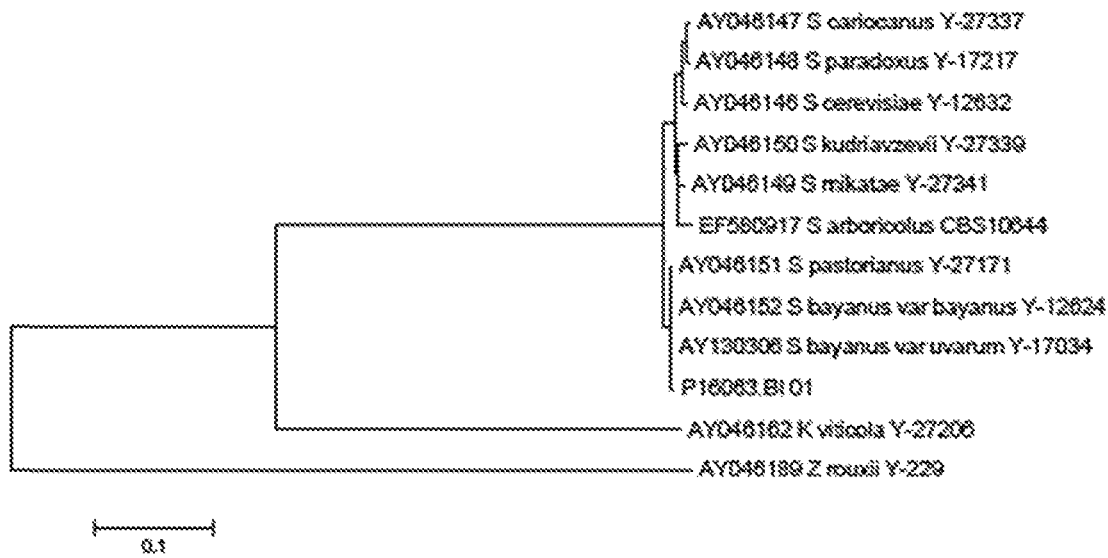
FIG. 1 reports the phylogenetic tree constructed based on ITS sequences, wherein the strain SERIUS of the present invention is indicated as P16063.BI01.

EXAMPLE 1—ISOLATION AND SELECTION STEPS FOR THE STRAIN ACCORDING TO THE INVENTION 1.1 Sampling Sampling has been conducted by collecting flowers during springtime, in an area of the Veneto region with high grape-wine producing activity.

Collection has been performed by avoiding touching the flowers with bare hand at all stages, and periodically sterilising the scissors, with the aim of limiting contamination as much as possible.

Flowers have been harvested in sufficient quantities to fill an appropriately sealed sterile bag. Upon arrival in the laboratory, the flowers have been transferred into sterile flasks containing 200 ml of synthetic must, previously prepared in distilled water, adjusted to pH 3.2 using KOH, and sterilised by filtration, the composition of which is reported in table 1.

TABLE 1

| Component category | Component | Dose per litre |
| --- | --- | --- |
| Macroelements | $CaCl_2$ | 0.1 g |
|  | NaCl | 0.1 g |
|  | $KH_2PO_4$ | 1 g |
|  | $MgSO_4 \times 7H_2O$ | 0.5 g |
|  | Tartaric acid | 3 g |
| Microelements | $NaMoO_4 \times 2H_2O$ | 0.2 mg |
|  | $ZnSO_4 \times 7H_2O$ | 0.4 mg |
|  | $H_3BO_3$ | 0.5 mg |
|  | $CuSO_4 \times 5H_2O$ | 0.04 mg |
|  | KI | 0.1 mg |
|  | $FeCl_3 \times 6H_2O$ | 0.4 mg |
|  | $MnSO_4 \times H_2O$ | 0.4 mg |
| Vitamins | Pyridoxine hydrochloride | 400 µg |
|  | Thiamine hydrochloride | 400 µg |
|  | Inosite | 2000 µg |
|  | Biotin | 20 µg |
|  | Calcium pantothenate | 400 µg |
|  | Nicotinamide | 400 µg |
|  | p-Aminobenzoic acid | 200 µg |
| Varying components | $(NH_4)_2SO_4$ | 0.3 g |
|  | $(NH_4)_2HPO_4$ | 0.3 g |
|  | Glucose | 200 g |
|  | Casein hydrolysate | 0.2 g |
|  | Malic acid | 2 g |

In addition, the synthetic must has been supplemented with the antibiotic, oxytetracycline, at a concentration of 0.1 mg/ml, so as to avoid any bacterial proliferation. The preparations have then been overlaid with sterile paraffin oil in order to avoid the formation of mould. The flasks have been sealed using a bored silicone bung, into which a Pasteur pipette, curved at the upper end, has been inserted. This has the purpose of avoiding potential contamination with microorganisms present in the environment, and allowing $CO_2$ to vent with no loss of water vapour. The flasks have been placed in an incubator at a constant temperature of between 22° C. and 25° C.

Progress of the fermentation has been monitored by measuring the drop in weight for each flask (an indicator of fermentation of the sugars to $CO_2$ and hence the progress of the fermentation).

1.2 Isolation of the Strains from the Samples

On completion of fermentation, 10 ml of product have been removed from each flask, a first 1:10 serial dilution has been performed, from which 1 ml has been removed and 5 subsequent serial dilutions (1:10) in Ringer's solution have been performed; 100 μl of the final three dilutions have then been seeded by spreading on WL agar medium (4.0 g/l yeast extract, 5.0 g/l tryptone, 50 g/l glucose, 550 mg/l potassium phosphate monobasic, 425 mg/l potassium chloride, 125 mg/l calcium chloride, 125 mg/l magnesium sulphate, 2.5 mg/l iron chloride, 2.5 mg/l manganese sulphate, 22 mg/l bromocresol green, 20 g/l agar) suitably sterilised by autoclave and adjusted to a final pH of 5.5±2. The plates have then been incubated at 28° C. for 3 days under aerobic conditions. In this medium, yeast colonies of the genus *Saccharomyces* appear with varying colour ranging from cream to light green, with a smooth-opaque surface and a creamy consistency. Yeast counting has revealed a *Saccharomyces* concentration of about $10^7$ CFU/ml, with the presence of both white and green colonies, with a smooth-opaque surface and a creamy consistency.

1.3 Purification and Storage of the Isolates

Colonies picked from the isolation plates have been reseeded on WL agar growth medium, the composition of which has been specified at point 1.2 of example 1. The procedure has been repeated at least twice, so as to be certain that each isolate originates from a single colony. The pure cultures obtained following the final passage on plates have been picked using a sterile loop and then cryopreserved at −80° C. following the addition of glycerol to 40% (w/w). On plates, the strain, subsequently identified as *Saccharomyces bayanus* subsp. *uvarum*, appears as small colonies, with an intense green colour, while strains attributable to the species *Saccharomyces cerevisiae* come from larger colonies, with a creamy consistency, coloured white or tending towards light green.

1.4 Identification of the Isolates at the Species and Strain Level

The presumed colonies of the yeasts *Saccharomyces* have been identified at the species level by means of RAPD-PCR using the M13 primer, according to the method described by Andrighetto et al. in 2000. In the analysis and subsequent processing of amplification profiles for the yeasts isolated from flowers, Type and reference strains from various yeast species of oenological and non-oenological interest have also been included. Comparison of the profiles has made it possible to recognise yeasts attributable to the species *S. cerevisiae* and *S. bayanus*.

To be able to discriminate at the strain level, two techniques have been used:
1) Analysis of mitochondrial DNA restriction profiles;
2) Analysis of microsatellites;
which shall be described in detail in the executive examples in section 1.6.

It is not excluded that the implementation of said genetic techniques may be performed using methods in themselves known to those skilled in the sector and that, therefore, the technical indications described herein may vary from that reported in the aforementioned examples.

1.5 Technological Characterisation of the Strains Isolated

In order to assess the fermentation characteristics, each of the yeasts selected has been subjected to fermentation testing, using natural or synthetic must according to the composition described in table 1.

The inoculum has been prepared in synthetic or natural must (depending on whether the fermentative vigour evaluation test was performed on synthetic must or natural must), starting from a wire loop pick taken from a slant or plate growth culture, and has been then incubated at 25° C. for 24 hours. Subsequently, this has been inoculated in the region of 10% in synthetic or natural must with a final volume of 200 ml, in flasks sealed with a centre-bored silicone bung, into which has been inserted a Pasteur pipette, bent so as to allow the venting of carbon dioxide with no loss of water vapour.

The drop in weight due to the loss of $CO_2$ from the flasks, set up for fermentation testing, has been monitored daily until completion of fermentation, corresponding to the phase where the drop in weight has remained constant for several days. For each isolate grown, the ability to produce foam during fermentation has been assessed by means of visual evaluation. Again, by means of visual evaluation, the growth method has been assessed for the strain during fermentation (pulverulent or flocculent).

Finally, for the evaluation of hydrogen sulphide production, each isolate has been seeded on Biggy agar medium (Bismuth Glucose Glycine Yeast Agar: 5 g/l bismuth ammonium citrate, 3 g/l sodium sulphite, 10 g/l glucose, 10 g/l glycine, 1 g/l yeast extract, 16 g/l agar, pH 6.8±0.2) and incubated at 25° C. for 5 days, after which, the colour of the colonies grown on the plates has been assessed. The quantity of hydrogen sulphide is directly proportional to the intensity of the colour, due to the creation of bismuth sulphite (dark brown if present in significant quantities). The technological characterisation of the isolates from flowers has made it possible to identify certain *Saccharomyces* yeast strains, including the strain *Saccharomyces bayanus* subsp. *uvarum* SERIUS, endowed with promising oenological characteristics.

1.6 Genetic Characterisation at the Strain Level

In order to achieve characterisation at the strain level, two techniques have been used:
Analysis of mitochondrial DNA restriction profiles;
Analysis of microsatellites.

Figure 2:
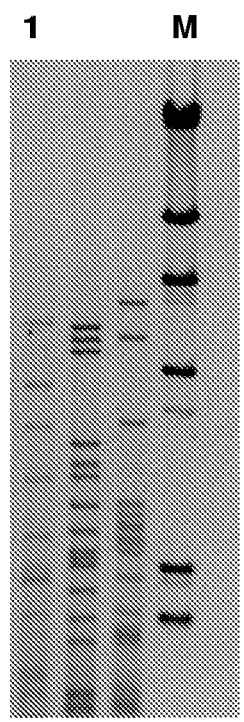
FIG. 2 shows the mitochondrial DNA restriction profile for the strain of the invention, obtained using the enzyme Hinf I, indicated by the number 1), wherein the profile indicated as M corresponds to the molecular weight marker.

Analysis of restriction profiles has been performed by following the method reported in Zilio et al. in 1998, using the restriction enzyme Hinf I. Separation of the linear DNA fragments has been obtained through electrophoresis on 1% agarose gel. Comparison of the restriction profiles has been performed using the software GelComparII (Applied Maths, Belgium) which, by means of the construction of a matrix, is capable of calculating the level of similarity between profiles and expressing the results graphically as a dendrogram. The mitochondrial DNA restriction profile for the strain SERIUS of the invention, obtained using the enzyme Hinf I, is shown in FIG. 2.

Microsatellite analysis envisages the use of PCR technique with primers that are complimentary to regions of the DNA known as microsatellites, which are small sequences of tandem repeat DNA (from one to six bases) varying in the number of repetitions, and may also be localised inside genomic coding regions (Legras, 2005). They are extremely variable in length, as a result of DNA replication errors, and therefore display a certain degree of polymorphism between individuals in the same species. Microsatellite polymorphism analysis is a highly reproducible method because specific primers and high annealing temperatures are used for their amplification. For characterisation of the strain *S. bayanus* subsp. *uvarum* SERIUS, the eight most variable loci described by Masneuf-Pomarede et al. in 2016 have been considered, and a reaction has been performed for each locus named: SuYIL130W (16 allelic forms), SuYHR102W (8 allelic forms), SuYKR045C (10 allelic forms), SuHTZ1PLB3 (7 allelic forms), SuARS409 (5 allelic forms), SuYHR042-043 (5 allelic forms), SuYBR049C (5 allelic forms), SuYGC170W (4 allelic forms).

The reaction has been conducted in a volume of 20 µl using 1 U of DNA polymerase in 1× buffer, with the addition of magnesium chloride ($MgCl_2$) at a concentration of 1.5 mM, nucleotide triphosphates (dNTPs) at a concentration of 200 µM and 1 µM for each of the primers for each reaction.

Amplification has been performed in a Mastercycler *Nexus* Gradient (Eppendorf) with a unique thermal program for all amplification reactions, with the exception of the annealing temperature (Ta). The thermal protocol used is reported in table 2 below (the number of repetitions for each cycle is reported in parentheses).

TABLE 2

| Amplification protocol | | |
|---|---|---|
| cycle | temperature | duration |
| Cycle1 (1x) | 94° C. | 5 min |
| Cycle2 (30x) | 94° C. | 30 s |
|  | Ta ° C. | 30 s |
|  | 72° C. | 30 s |
| Cycle3 (1x) | 72° C. | 10 min |

The Ta used has been set at 55° C. for PCR reactions concerning the loci SuYIL130W, SuYHR102W and SuYGC170W; while the aforementioned Ta has been set at 50° C. for the PCR reactions concerning the loci SuYKR045C, SuHTZ1PLB3, SuARS409, SuYHR042-043 and SuYBR049C.

Figure 3:
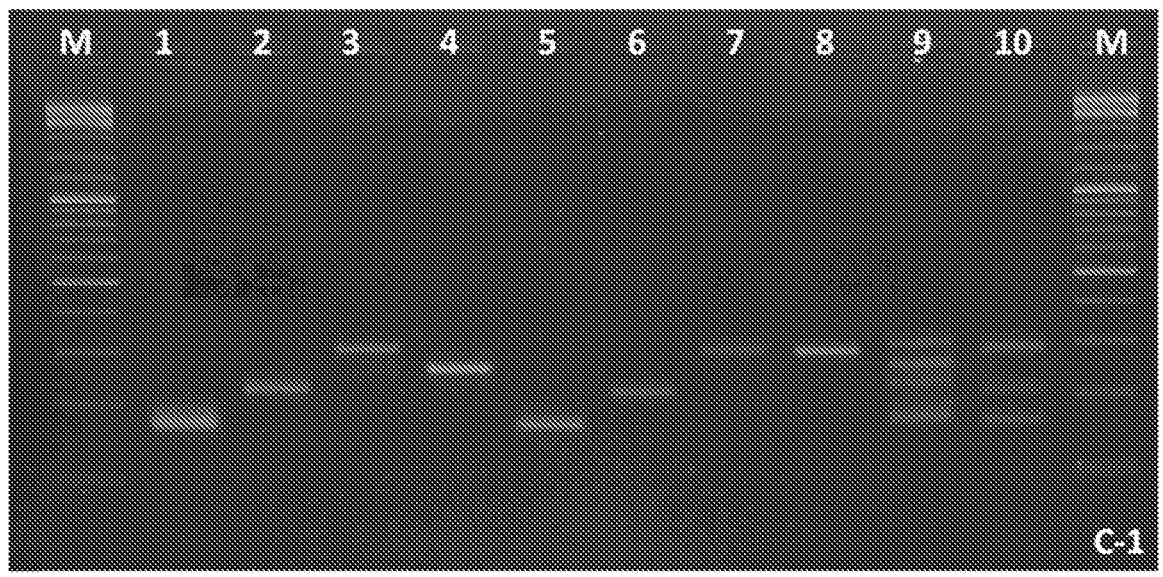
FIG. 3 shows the agarose gel electrophoresis results for each PCR product obtained by amplification of DNA from the strain SERIUS at the eight most variable loci. The loading order shown is as follows:
(M) O'Gene Ruler marker (Fermentas),
(1) PCR product for the locus SuYIL130W,
(2) PCR product for the locus SuYHR102W,
(3) PCR product for the locus SuYKR045C,
(4) PCR product for the locus SuHTZ1PLB3,
(5) PCR product for the locus SuARS409,
(6) PCR product for the locus SuYHR042-043,
(7) PCR product for the locus SuYBR049C,
(8) PCR product for the locus SuYGC170W,
(9) the profile obtained by loading the amplification products obtained in the individual PCR reactions for the loci SuYIL130W, SuYHR102W, SuYKR045C and SuHTZ1PLB3 in the same well, (10) the profile obtained by loading the amplification products obtained in the individual PCR reactions for the loci SuARS409, SuYHR042-043, SuYBR049C and SuYGC170W in the same well.

Amplification and agarose gel electrophoresis migration of the PCR products relating to the eight most variable loci in *S. bayanus* var. *uvarum*, have made it possible, for the strain of *Saccharomyces bayanus* subsp. *uvarum* SERIUS, to define the unique and characteristic profile reposted in FIG. 3.

In addition to the individual PCR reaction, the eight aforementioned loci have also been analysed by means of two multiplex reactions, capable of the simultaneous amplification of three and five loci, respectively.

In particular, two multiplex-PCR reactions have been used: multiplex-PCR1 allows analysis of the DNA-microsatellite profile for loci SuYIL130W, SuYHR102W and SuYGC170W, and multiplex-PCR2 allows attainment of the DNA-microsatellite profile for loci SuYKR045C, SuHTZ1PLB3, SuARS409, SuYHR042-043 and SuYBR049C.

The two multiplex-PCR reactions have been conducted in a volume of 20 µl, using 1.5 U and 1 U of DNA polymerase respectively in 1× buffer with the addition of magnesium chloride ($MgCl_2$) at a concentration of 1.5 mM and nucleotide triphosphates (dNTPs) at a concentration of 200 µM. The concentration of the primers has been optimised as follows.

In the case of multiplex-PCR1, the two primers for locus SuYIL130W have been added at a concentration of 0.25 µM, the two primers for locus SuYHR102W at a concentration of 0.75 µM, while the two primers for locus SuYGC170W at a concentration of 1 µM.

In the case of multiplex-PCR2, the two primers for loci SuYKR045C, SuHTZ1PLB3, SuARS409, SuYHR042-043 and SuYBR049C have been applied at a concentration of 0.5 µM.

Amplification has been performed in a Mastercycler *Nexus* Gradient (Eppendorf) with a unique thermal program for all amplification reactions, with the exception of the annealing temperature (Ta). The thermal program used is reported in table 3 below (the number of repetitions for each cycle is reported in parentheses).

TABLE 3

| Amplification protocol | | |
|---|---|---|
| cycle | temperature | duration |
| Cycle 1 (1x) | 94° C. | 5 min |
| Cycle 2 (30x) | 94° C. | 30 s |
|  | Ta ° C. | 30 s |
|  | 72° C. | 30 s |
| Cycle 3 (1x) | 72° C. | 10 min |

In the case of multiplex-PCR1 the Ta used has been 55° C., while in the case of multiplex-PCR 2 it has been 50° C.

Figure 4:
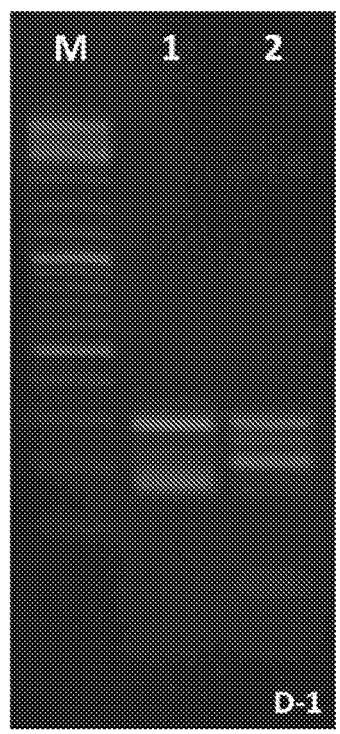
FIG. 4 reports the electrophoresis result for the 2 multiplex PCR reactions on 3% agarose gel, in the loading order corresponding to the following:
(M) O'Gene Ruler marker (Fermentas),
(1) multiplex-PCR1 product for the loci SuYIL130W, SuYHR102W and SuYGC170W,
(2) multiplex-PCR2 product for the loci SuYKR045C, SuHTZ1PLB3, SuARS409, SuYHR042-043 and SuYBR049C.

The profiles obtained from the aforementioned analysis are reported in FIG. 4.

Furthermore, characterisation of the strain of the invention has also been performed by means of capillary electrophoresis based on amplification of the four loci which, according to data in the literature, are characterised by a greater number of allelic forms.

Advantageously, said characterisation has made it possible to define the exact size of the PCR products for the 4 loci considered.

The loci considered are the following: SuYIL130W, SuYHR102W, SuYKR045C and SuHTZ1PLB3. Amplification has been performed according to the protocol reported previously, with the single variant consisting of modification of the 5' end of the forward primers with a fluorescent molecule. In particular, SuYIL130W-FW and SuYKR045C-FW have been labelled with Hexachloro-fluorescein (HEX), while SuHTZ1PLB3-FW and SuYHR102W-FW have been labelled with 6-carboxyfluorescein (FAM).

Analysis of the capillary profile has been performed using the D filter, with internal reference ROX. Interpretation has been performed using the software Peak Scanner 2.0, with the following parameters: "size standard: GS500 (−250)" and "analysis method: sizing default—NPP". The results obtained, namely the sizes of the fragments, are reported in table 4 and are expressed in base pairs (bp) with an error of +/−1 bp.

TABLE 4

| Strain | SuYIL130W | SuYHR102W | SuYKR045C | SuHTZ1PLB3 |
|---|---|---|---|---|
| *Saccharomyces bayanus* var. *uvarum* SERIUS | 179 | 219 | 300 | 259 |

It is not excluded that the implementation of said genetic techniques may be performed using methods in themselves known to those skilled in the sector and that, therefore, the aforementioned technical indications may vary from that reported.

EXAMPLE 2—TECHNOLOGICAL CHARACTERISATION OF THE YEAST 2.1 Production of Hydrogen Sulphide Production of hydrogen sulphide by the strain SERIUS has been evaluated by means of incubation at 25° C. for 5 days in Biggy Agar medium (1 g/l yeast extract, 10 g/l glycine, 10 g/l dextrose, 5 g/l bismuth ammonium citrate, 3 g/l sodium sulphite, 16 g/l agar). On completion of incubation, in this medium, the colonies appear with different colours, based on the quantity of hydrogen sulphide they produce. Colonies that are dark brown in colour indicate high hydrogen sulphide production, colonies that are clear brown-beige in colour indicate moderate production, while white colonies are characterised in that they are incapable of producing it. Following incubation on Biggy agar medium, colonies of the strain of the invention appear white in colour, thus, under the conditions tested, the strain is incapable of producing $H_2S$. Testing has also been repeated by analysis of hydrogen sulphide production in Lead Acetate Agar medium (15 g/l peptone, 5 g/l proteose peptone, 1 g/l dextrose, 0.2 g/l lead acetate, 0.08 g/l sodium thiosulphate, 15 g/l agar) incubated at 25° C., and the results obtained have been analogous to those obtained with Biggy agar medium.

2.2 Fermentative Vigour

The fermentative vigour of the strain of the invention has been evaluated in both synthetic must, the characteristics of which are described in example 1, point 1.1, and in various types of natural white berry grapes and red berry grapes must. The inoculum has been prepared in synthetic or natural must (depending on whether the fermentative vigour evaluation test was performed on synthetic must or natural must), starting from a wire loop pick taken from a slant or plate growth culture, and has been then incubated at 25° C. for 24 hours. Subsequently, this has been inoculated in the region of 10% in synthetic or natural must with a final volume of 200 ml, in flasks sealed with a centre-bored silicone bung, into which has been inserted a Pasteur pipette, bent so as to allow the venting of carbon dioxide with no loss of water vapour. This way it has been possible to follow the progress of the fermentation by means of monitoring the drop in weight due to the production of $CO_2$, an indicator of fermentation of the sugars. Incubation has been conducted at a constant temperature of 25° C., and evaluation of the weight loss has been performed every 1-2 days, until achieving constant weight. Using the data collected, growth curves have been prepared, and the fermentative vigour of the strain *Saccharomyces bayanus* var. *uvarum* SERIUS has been compared with the fermentative vigour of commercial strains of *Saccharomyces bayanus* and *cerevisiae*. In the various fermentation tests, the strain of the invention has displayed a good ability for fermentation, with mean loss of weight values at 2 and 7 days that are analogous to those observed with commercial yeasts of the species *Saccharomyces cerevisiae*, and with fermentation completion times varying depending on the type of must used (from 10 to 15 days).

The fermentative vigour of the strain has also been evaluated in natural must obtained from Trebbiano grapes, by means of incubation at temperatures of 12, 15 and 24° C. Analysis reveals that the strain has good fermentative ability, even at temperatures of 12° C. and 15° C.

Advantageously, this latter characteristic of the strain of the invention allows its use in wine fermentations at low temperatures, thus increasing the possibility of activating specific biochemical reactions leading to the production of aromatic compounds having a positive influence on the organoleptic qualities of the wine produced.

2.3 Production of Glycerol

Glycerol production has been evaluated by means of HPLC (Jasco RI 930 detector, Rezex™ ROA-Organic Acid H+8% column (300×7.8 mm) in natural white berry grapes and red berry grapes must inoculated with the strain SERIUS, with incubation at 25° C. until completion of fermentation.

In addition, comparative tests have been set up where a commercial strain of *Saccharomyces cerevisiae* has been inoculated. The results obtained are reported in table 5, where the quantity of glycerol produced is expressed in g/l. It may be observed that the strain of the invention shows significant glycerol production, higher on average than the quantity of glycerol produced in the same must by commercial yeast used as a comparison.

TABLE 5

| | White berry musts | | | Red berry musts | | |
|---|---|---|---|---|---|---|
| Strain | Garganega | Kerner | Trebbiano | Merlot | Nerello Mascalese | Nero d'Avola |
| SERIUS | 8.8 | 10.6 | 8.7 | 9.1 | 9.8 | 9.5 |
| Commercial *S. cerevisiae* | 6.8 | 7.5 | 5.8 | 8.1 | 8.1 | 6.5 |

2.4 Production of Malic Acid

The strain of the invention has been tested for the ability to produce malic acid in natural white berry and red berry must, following incubation at 25° C. until fermentation completion. In particular, the quantity of malic acid present in the various musts before and after fermentation using the aforementioned strain has been assessed by means of HPLC Jasco UV 975 detector, Resex™ ROA-Organic Acid H+8% column (300×7.8 mm). Analogously to example 2.3, comparative tests have been conducted with an inoculum of the commercial strain of *Saccharomyces cerevisiae* used previously. The results obtained are reported in table 6 where the quantity of malic acid is expressed in g/l. It may be observed that the strain SERIUS is capable of producing malic acid, even though with varying efficiency, in 5 of the 6 musts tested, unlike the commercial strain, which is characterised by the ability to partially degrade malic acid.

TABLE 6

| Must | Prior to fermentation | End of fermentation SERIUS | End of fermentation commercial *S. cerevisiae* |
|---|---|---|---|
| Garganega | 1.3 | 3.9 | 1.2 |
| Kerner | 3.0 | 4.0 | 2.1 |
| Trebbiano | 1.8 | 1.3 | 1.5 |
| Merlot | 2.3 | 3.0 | 1.2 |
| Nerello Mascalese | 2.8 | 3.1 | 1.4 |
| Nero d'Avola | 1.5 | 2.5 | 1.2 |

2.5 Production of Volatile Acidity

The ability to produce acetic acid has been evaluated by means of HPLC Jasco RI 930 detector, Rezex™ ROA-Organic Acid H+8% (300×7.8 mm) column in natural white berry and red berry must inoculated with the strain SERIUS, incubated at 25° C. until completion of fermentation. Comparative tests inoculated with a commercial strain of *Saccharomyces cerevisiae* have also been set up. The results obtained are reported in table 7, where the acetic acid production values, expressed in g/l, are reported, demonstrating that the strain of the invention is characterised by the ability to produce little volatile acidity.

TABLE 7

| Must | Prior to fermentation | End of fermentation SERIUS | End of fermentation commercial *S. cerevisiae* |
|---|---|---|---|
| Garganega | 0 | 0.11 | 0.29 |
| Kerner | 0 | 0.22 | 0.18 |
| Trebbiano | 0 | 0.16 | 0.23 |
| Merlot | 0 | 0.30 | 0.39 |
| Nerello Mascalese | 0 | 0.22 | 0.46 |
| Nero d'Avola | 0 | 0.1 | 0.18 |

2.6 Killer Activity

The presence of killer activity in the yeast SERIUS has been studied using YEPD agar medium, prepared by means of the prior inoculation and overnight incubation of a culture of a sensitive indicator strain. Operatively, after having left said plates including the indicator strain to dry, 10 µl of a fresh culture of the strain SERIUS has been deposited on them and the same plates have been left to incubate for 48 hours at 25° C. Subsequently, on completion of the incubation period, killer activity has been detected by the appearance of "inhibition halos" (an inhibition halo is understood as being an area with the absence of growth) around the colony of the strain under test.

With regard to the strain SERIUS, killer activity has been tested in relation to 10 oenological yeast strains belonging to the species *S. cerevisiae* and *S. bayanus* respectively.

The analysis has shown that none of the yeasts tested has been inhibited by the strain of the invention. In addition, none of the 10 yeasts tested has demonstrated the ability to inhibit the strain SERIUS.

2.7 Resistance to Copper and Resistance to Sulphur Dioxide

Copper resistance has been assayed by means of growth in synthetic YNB (Yeast Nitrogen Base) medium, characterised by the absence of aminoacids and the presence of 6.7 g/l sulphate, 20 g/l glucose and 20 g/l agar, supplemented with various concentrations of $CuSO_4$ (50, 100, 200, 300 µmol/l respectively). With regard to sulphur dioxide resistance, this has been evaluated by means of growth in agarised must supplemented with potassium metabisulphite in such concentrations as to give a final $SO_2$ concentration essentially corresponding to 50, 100, 200 and 300 ppm. Both analyses described above have been performed by means of incubation of the strain SERIUS in previously prepared media for 48 hours at 26° C., and a visible growth has been evaluated on plates.

The results obtained are reported in table 8, expressed as MTC (Maximum Tolerated Concentration, of copper or sulphur dioxide respectively). As may be observed from the following table, the strain SERIUS demonstrates the ability to grow in the presence of 300 ppm $SO_2$ and 300 µmol/l copper.

By way of comparison, the aforementioned tests have also been conducted on 5 commercially available strains of *S. cerevisiae* for oenological use.

TABLE 8

| Strain | MTC $SO_2$ (ppm) | MTC $CuSO_4$ (µmol/l) |
|---|---|---|
| SERIUS | 300 | 300 |
| Commercial *S. cerevisiae* 1 | 300 | 50 |
| Commercial *S. cerevisiae* 2 | 300 | 50 |
| Commercial *S. cerevisiae* 3 | 50 | 50 |
| Commercial *S. cerevisiae* 4 | 300 | 100 |
| Commercial *S. cerevisiae* 5 | 300 | 100 |

2.8 Tolerance to Ethanol

Ethanol tolerance has been assayed using agarised must including varying concentrations of ethanol, corresponding to 12, 14, 16 and 18% respectively. The strain SERIUS has been incubated in said medium for 48 hours at 26° C., on completion of which, visible growth has been evaluated on plates.

The analysis shows that the strain SERIUS has an MTC value for ethanol equal to 16% vol/vol.

2.9 Carbon Source Use

The ability of the strain SERIUS to assimilate/ferment various carbon source compounds has been evaluated by means of growth of the aforementioned strain in media containing yeast extract (10 g/l), peptone (20 g/l) and sugar/organic acid at a concentration of 20 g/l.

The analysis has shown that the strain SERIUS is capable of using such organic compounds as galactose, raffinose, maltose and gluconic acid.

2.10 Volatile Compound Production and Aromatic Profile

The production of acetaldehyde, methyl acetate, ethyl acetate and higher alcohols has been evaluated on completion of fermentation in samples of Trebbiano must inoculated and fermented using the strain SERIUS, and in samples of the same must inoculated and fermented with a commercial *Saccharomyces cerevisiae* yeast. Determination of the volatile compounds has been conducted by means of gas chromatography, injecting samples of suitably distilled wine directly into a ZB-WAX Plus polar column (stationary phase of polyethylene glycol, FID—Flame Ionization Detector).

The results obtained, expressed in mg/l, are reported in Table 9.

TABLE 9

| Metabolite (mg/l) | SERIUS | COMM 1 |
|---|---|---|
| Acetaldehyde | 52 | 42 |
| Methyl acetate | <2 | <2 |
| Ethyl acetate | 41 | 25 |
| Methanol | 0.05 | 0.04 |
| 2-Butanol | <2 | <2 |
| N-Propanol | 55 | 23 |
| Isobutanol | 43 | 40 |
| Isoamyl acetate | <2 | <2 |
| N-Butanol | <2 | <2 |
| Isoamyls | 69 | 120 |

The strain SERIUS produces slightly higher quantities of acetaldehyde with respect to those produced by the commercial yeast used for comparison, concentrations however that are not compromising for the quality of the wines. Indeed, it is known that a low concentration of said compound in wine gives a pleasing fruity aroma, while at increasing concentrations, the wine has a tendency to release a pungent and irritant odour, so as to become unmarketable when the acetaldehyde concentration exceeds 500 mg/l.

With regard to higher alcohols, the strain SERIUS produces N-propanol in greater quantities compared to the commercial reference strain, while it produces similar quantities of isobutanol; however, these alcohols do not play a significant olfactory role in wine.

On the other hand, in comparison to the commercial *S. cerevisiae* strain, the strain SERIUS produces a lower quantity of isoamyl alcohol; the latter higher alcohol plays an important role as it results in the so-called "amylic" odour, which is considered very negative from an olfactory viewpoint.

The aromatic profile of the strain SERIUS has been evaluated by means of the solid phase extraction (SPE) technique used on Trebbiano grapes must, obtained following incubation with the aforementioned strain at 25° C. for a length of time sufficient to reach the completion of fermentation. Furthermore, analogously, two commercial *S. cerevisiae* strains have been assayed by way of comparison.

Operatively, 10 ml of each strain sampled (SERIUS, and the two commercial strains) have been diluted with 30 ml of water and spiked with the internal standard (1-heptanol) and absorbed onto the SPE C18 column. Elution has been performed using dichloromethane, and the eluate, reduced to a small volume, has been injected into the Shimadzu GC2010/QP2010 GC/MS system. Identification of the resulting compounds has been performed by means of searching the latest versions of the Whiley and NBS libraries available at the time of preparation of the present application.

From the present analysis, it is demonstrated that the strain of the invention allows the attainment of a wine with concentrations of fatty acids (isovaleric acid, hexanoic acid, octanoic acid, butanoic acid, decanoic acid) that are on average 2-3 fold less than those detected in wines obtained with the two commercial strains. It is known that certain medium and long-chain fatty acids (C6, C8, C10, C12) can have inhibitory effects with regard to the fermentative activity of yeasts. In particular, even at low concentrations (a few milligrams/litre), decanoic acid (C10) shows significant antagonistic activity with regard to fermentation processes.

An additional characteristic differentiating the strain SERIUS from the two commercial strains used by way of comparison is the significantly higher production (30 fold greater on average) of phenyl ethyl esters of octanoic acid, volatile compounds giving the aroma typical of green cocoa. Finally, the wine obtained with the yeast SERIUS shows reduced concentrations of pyrazine and piperazine, molecules responsible for herb and plant aromas.

EXAMPLE 3—OENOLOGICAL CHARACTERISATION OF THE YEAST, VINIFICATION TESTS

The strain of the invention has been tested by means of winery vinification tests on red berry grapes and white berry grapes musts.

The production process used has been the fed-batch type, followed by the concentration of the culture by means of centrifugation. Then, a yeast biomass has been prepared in cream form with a dry substance content essentially equal to 22%, and a yeast concentration of about 10 billion CFU/g.

For subsequent inoculation of the must, the biomass has been resuspended in a vinous suspension consisting of yeast, must and activators.

In particular, for use in a 5000-litre tank, 1 kg of cream-form biomass of the yeast SERIUS has been suspended at a temperature of 25° C. in 200 litres of must, supplemented with activators at the working concentrations recommended by the manufacturer, and known commercially. The suspension has been kept in motion using a stirrer or racking pump for ¾ hours. Subsequently, said suspension has been added to the must by means of racking.

3.1 Test Using Traminer Grape Must with Must Acidification

The yeast of the invention has been tested with Traminer (white berry) grape must in a winery in a 50 hl tank.

The yeast, prepared in fresh cream form, has been used at a dose of 20 g/hl.

The addition to the must of 100 g/hl of yeast autolysate and 140 g/hl of tartaric acid has been followed by inoculation with the strain SERIUS, prepared previously according to the method described in the general section. Fermentation has been conducted at 13° C. for a period of 19 days.

Table 10 reports the analytical data concerning the must prior to yeast inoculation and the wine on completion of fermentation. It may be observed how the strain produces advantageously high quantities of malic acid and glycerol, and at the same time, shows low volatile acidity production.

With regard to the aromatic profile, on completion of fermentation, greater floral complexity is noted, synergistic with the terpene profile, in comparison to commercial yeast.

TABLE 10

| | Must | Wine |
|---|---|---|
| Total acidity g/l | 4.80 | 6.57 |
| pH | 3.47 | 3.46 |

TABLE 10-continued

|  | Must | Wine |
| --- | --- | --- |
| Malic acid g/l | 1.09 | 1.92 |
| Citric acid g/l | 0.12 | 0.2 |
| Lactic acid g/l | 0.10 | 0.22 |
| Glucose g/l | 88.1 | 0.4 |
| Fructose g/l | 106.9 | 6.5 |
| Succinic acid g/l | 0.07 | 0.99 |
| Glycerol g/l | 3.47 | 11.45 |
| Acetic acid g/l | 0.21 | 0.09 |
| Ethanol % | 2.82 | 14.11 |

3.2 Test Using Traminer Grape Must without Must Acidification

The yeast SERIUS has been tested with Traminer (white berry) grape must in a winery in a 100 hl tank. The yeast has been prepared in fresh form (cream) and used at a dose of 20 g/hl. Preparation of the inoculum has been carried out as described previously. Prior to inoculation, 90 g/hl of yeast autolysate have been added to the must. The must has not been acidified with tartaric acid. Fermentation has been conducted at 17° C. for a period of 7 days.

Table 11 reports the analytical data concerning the must prior to yeast inoculation and the wine on completion of fermentation.

The results obtained highlight the ability of the strain SERIUS to produce high quantities of glycerol and low volatile acidity. With respect to the previous example in Traminer must, wherein malic acid production has been observed, in this case, malic acid production is not observed. It should be noted that the must in example 3.1 had been acidified with tartaric acid, while the must in this example has not been subjected to supplementing with tartaric acid. Hence, the production of malic acid by the strain SERIUS seems to be correlated with tartaric acid acidification of the must.

Olfactory analysis confirms the results highlighted in the example described at point 3.1.

TABLE 11

|  | Must | Wine |
| --- | --- | --- |
| Total acidity g/l | 6.70 | 6.29 |
| pH | 3.26 | 3.30 |
| Malic acid g/l | 1.24 | 1.10 |
| Citric acid g/l | 0.16 | 0.27 |
| Lactic acid g/l |  | 0.23 |
| Glucose g/l | 81.5 | 0.3 |
| Fructose g/l | 100.3 | 5.7 |
| Succinic acid g/l |  | 0.55 |
| Glycerol g/l | 3.54 | 10.15 |
| Acetic acid g/l | 0.08 | 0.15 |
| Ethanol % | 2.72 | 13.10 |

3.3 Test Using Garganega Grape Must with Must Acidification

The strain SERIUS has been tested with Garganega (white berry) grape must in a winery in a 150 hl tank. The yeast has been prepared in fresh form (cream) and used at a dose of 20 g/hl. Preparation of the inoculum has been carried out as described above. Prior to inoculation, 120 g/hl of yeast autolysate and 120 g/hl of tartaric acid have been added to the must. Fermentation has been conducted at 16° C. for a duration of 15 days.

The results obtained are reported in table 12. The ability of the strain SERIUS to produce malic acid, high quantities of glycerol and low volatile acidity is highlighted.

With regard to the aromatic profile, marked floral notes with a hint of glycine are reported.

TABLE 12

|  | Must | Wine |
| --- | --- | --- |
| Total acidity g/l | 4.72 | 8.85 |
| pH | 3.53 | 3.27 |
| Malic acid g/l | 0.97 | 2.70 |
| Citric acid g/l | 0.16 | 0.23 |
| Lactic acid g/l | 0.01 | 0.24 |
| Glucose g/l | 80.6 | 0.3 |
| Fructose g/l | 90.4 | 9.2 |
| Succinic acid g/l | 0.02 | 1.36 |
| Glycerol g/l | 1.55 | 10.34 |
| Acetic acid g/l | 0.02 | 0.16 |
| Ethanol % | 1.21 | 11.23 |

3.4 Testing Using Garganega Grape Must without Must Acidification

The strain SERIUS has been tested with Garganega (white berry) grape must in a winery in a 100 hl tank. The yeast has been prepared in fresh form (cream) and used at a dose of 20 g/hl. Preparation of the inoculum has been carried out as described above. Prior to inoculation, 120 g/hl of yeast autolysate have been added to the must. The must has been acidified with tartaric acid. Fermentation has been conducted at 16° C. for a period of 12 days.

Table 13 reports the results obtained with the must prior to inoculation, and of the wine on completion of fermentation.

It may be observed how the strain has the ability to produce high quantities of glycerol with low volatile acidity production. Again, in this case, in the absence of acidification of the must with tartaric acid, no malic acid production is reported.

The aromatic profile confirms that observed in example 3.3, namely the presence of marked floral notes with a hint of glycine.

TABLE 13

|  | Must | Wine |
| --- | --- | --- |
| Total acidity g/l | 6.36 | 6.44 |
| pH | 3.47 | 3.59 |
| Malic acid g/l | 2.86 | 2.64 |
| Citric acid g/l | 0.40 | 0.46 |
| Lactic acid g/l | 0.02 | 0.13 |
| Glucose g/l | 96.9 | 0.3 |
| Fructose g/l | 105.8 | 3.7 |
| Succinic acid g/l | 0.08 | 0.56 |
| Glycerol g/l | 1.68 | 9.74 |
| Acetic acid g/l | 0.07 | 0.25 |
| Ethanol % | 1.35 | 13.60 |

3.5 Testing in Syrah, Petit Verdot, Cabernet Grapes Must with Must Acidification The strain SERIUS has been tested with Syrah, Petit Verdot, Cabernet (red berry) grape must in a winery in a 100 hl tank. The yeast has been prepared in fresh form (cream) and used at a dose of 20 g/hl. Preparation of the inoculum has been carried out as described above. Prior to inoculation, 150 g/hl of yeast autolysate and 100 g/hl of tartaric acid have been added to the must. Fermentation has been conducted at 20° C. for a period of 10 days.

Table 14 reports the results obtained with the must prior to inoculation, and of the wine on completion of fermentation. Again, in this case, the ability of the strain SERIUS to produce malic acid and high quantities of glycerol is observed.

With regard to the aromatic profile, the wine produced using the strain SERIUS has distinct blueberry, raspberry and wild strawberry notes.

TABLE 14

|  | Must | Wine |
|---|---|---|
| Total acidity g/l | 4.85 | 7.48 |
| pH | 3.78 | 3.74 |
| Malic acid g/l | 1.37 | 3.70 |
| Citric acid g/l | 0.58 | 0.63 |
| Lactic acid g/l | 0.4 | 0.44 |
| Glucose g/l | 125.7 | 1.6 |
| Fructose g/l | 138.3 | 16 |
| Succinic acid g/l | 0.04 | 0.80 |
| Glycerol g/l | 2.2 | 12.46 |
| Acetic acid g/l | 0.19 | 0.15 |
| Ethanol % | 1.4 | 16.62 |

EXAMPLE 4—HYBRIDS OBTAINED FROM THE YEAST S. BAYANUS SUBSP. UVARUM SERIUS

The strain S. bayanus subsp. uvarum SERIUS may be used as the parental strain in order to obtain yeast hybrids with additional and improved oenological characteristics. The direct hybridisation technique has been chosen and a standard spore-spore conjugation protocol with slight modifications has been followed to obtain hybrids (Solieri et al., 2008). Initially, a sporulation study has been performed on the strains selected for hybridisation. Several culture media have been tested for this purpose. The spore viability and sporulation efficiency study has allowed the selection of SP medium (1% potassium acetate; 0.1% yeast extract; 0.05% glucose; 1.8% agar). Growth of the strain on SP at 25° C. for 7-10 days has been followed by partial digestion of the cell wall in order to allow subsequent separation of the spores from the ascii using a micromanipulator needle. The ascii, with the semi-digested cell wall, have been placed on one side of a YPD plate (2% glucose; 2% peptone; 1% yeast extract; 2% agar) and then subjected to micromanipulation. The spores of the two parental strains have been placed randomly next to one another. Continuous observation has allowed the identification of successful conjugation. Following incubation at 25° C. for 2-3 days, the colonies selected have been re-streaked on YPD medium. The following step has been the stabilisation of the strains (also performed on WL medium). Hybrids have then been confirmed by means of molecular analysis and have then been subjected to fermentation testing in must along with phenotypic analysis in order to verify their physiological characteristics and oenological potential.

EXAMPLE 5—PRODUCTION OF YEAST AUTOLYSATES STARTING FROM THE STRAIN S. BAYANUS SUBSP. UVARUM SERIUS

The strain S. bayanus subsp. uvarum SERIUS may be used to produce a yeast autolysate to be used as a fermentation activator in the production of wine and other alcoholic beverages. To this end, the yeast cream, prepared as described above, is subjected to appropriate heat treatment (40-60° C. for 12-48 hours). The autolysate obtained may be used as it is or further processed by means of appropriate filtration/centrifugation/decanting with the aim of separating the solid or liquid phases for subsequent suitable applications.

Hence, based on the above, the present invention has achieved all pre-set objectives.

In particular, the goal of providing a yeast strain of the species Saccharomyces bayanus subsp. uvarum, equipped with the technological and oenological characteristics allowing good fermentation of the must, allowing the production of a pleasing wine, is achieved.

Another goal achieved is that of providing a strain allowing the attainment of a wine characterised by high quantities of malic acid and glycerol, and at the same time not producing hydrogen sulphide during alcoholic fermentation.

Another goal achieved by the present invention concerns the possibility of using the strain SERIUS as the parental strain to obtain hybrid yeasts with novel oenological potential.

A further goal achieved concerns the possibility of using the strain forming the subject of the invention to obtain a yeast autolysate to be used as an activator of fermentation.

By no means a final goal of the invention achieved is the optimization of a perfected and rapid method for the selection of yeast strains for oenological use, particularly yeasts from the species Saccharomyces bayanus isolated from flowers.

BIBLIOGRAPHY

1. Andrighetto C., Psomas E., Tzanetakis N., Suzzi G., Lombardi A. (2000): Randomly Amplified Polymorphic DNA (RAPD) PCR for the identification of yeasts isolated from dairy products. Letters in Applied Microbiology, 30:5-9;
2. Cai J., Roberts I. N. and Collins M. D. (1996): Phylogenetic relationships among members of the ascomycetous yeast genera Brettanomyces, Debaryomices, Dekkera, and Kluyveromyces deduced by small-subunit rRNA gene sequences. Int. J. Syst. Bacteriol. 46: 542-549;
3. Castellari L., Ferruzzi M., Magrini A., Giudici P., Passarelli P., Zambonelli C. (1994): Unbalanced wine fermentation by cryotolerant vs. non-cryotolerant Saccharomyces strains Vitis, 33, 49-52;
4. Delfini C. (1995): Scienza e tecnica di microbiologia enologica. Edizioni II Lievito, Asti;
5. Esteve-Zarzoso B, et al. (1999): Identification of yeasts by RFLP analysis of the 5.8S rRNA gene and the two ribosomal internal transcribed spacers. Int J Syst Bacteriol 49 Pt 1:329-37;
6. Fleet G. H (2008): Wine yeasts for the future. FEMS Yeast Res 8; 979-995;
7. James S. A., Collins M. D. and Roberts I. N. (1996): Use of an rRNA internal transcribed spacer region to distinguish phylogenetically closely related species of the genera Zygosaccharomyces and Torulaspora. Int. J. Syst. Bacteriol. 46: 189-194;
8. Legras J. L., Ruh O., Merdinoglu D., Karst F. (2005): "Selection of hypervariable micro satellite loci for the characterization of Saccharomyces cerevisiae strains", International Journal of Food Microbiology 102: 73-83;
9. Masneuf-Pomarede I., Salin F., Bodin M., Coton E., Coton M., Jeune C. L., Legras J. L. (2016): Microsatellite analysis of Saccharomyces uvarum diversity. FEMS Yeast Res. 16(2): fow002;
10. Suzzi G, Tofalo R. (2014): Microbiologia Enologica Edagricole;
11. Pretorius I S (2000): Tailoring wine yeast for the new millennium: novel approaches to the ancient art of winemaking Yeast 16: 675±729;

12. Ribereau-Gayon P., Dubordieu D., Doneche B., Lonvaud A. (2000): Handbook of Enology Volume 1 The Microbiology of Wine and Vinification, John Wiley & Sons Ltd;
13. Solieri L, Antunez O, Perez-Ortin J E, Barrio E, Giudici P. (2008): Mitochondrial inheritance and fermentative oxidative balance in hybrids between *Saccharomyces cerevisiae* and *Saccharomyces uvarum* Yeast. 25(7):485-500;
14. Vaughan-*Martini* A. & *Martini* A. (2011): Chapter 61—*Saccharomyces* Meyen ex Reess (1870). In: The Yeasts (Fifth Edition). London: Elsevier;
15. Vincenzini M., Romano P. e Farris G. A. (2005): Microbiologia del vino. Edizioni Ambrosiana;
16. White T. J., Bruns T., Lee S. and Taylor J. (1990): PCR protocols. A guide to methods and applications. In Amplification and direct sequencing of fungal ribosomal RNA genes for phylogenetics, pp. 315-322. Innis M. A., Gelfand D. H., Sninsky J. J., White T. J. (Eds) Academic Press, San Diego;
17. Zambonelli C, *Soli* MG & Guerra D (1984): A study of H2S nonproducing strains of wine yeasts. Ann Microbiol 34: 7-15;
18. Zambonelli C., Tini V. and Castellari L. (2000). Guida all'uso dei lieviti selezionati in enologia (a cura del Centro Ricerche Produzioni Vegetali) Ed. agricole;
19. Zambonelli C. (2003): Microbiologia e Biotecnologia dei *Vini*. Edizioni Agricole;
20. Zilio F., Lombardi A., Galeotto A., Comi G. (1998): Profili di restrizione del DNA mitocondriale di ceppi di *Saccharomyces* isolati nella zona di produzione del vino Soave DOC. Riv. Vitic. Enolog. 3:33-41.

The invention claimed is:

1. A method of using a strain of *Saccharomyces bayanus* subsp. *uvarum* identified as SERIUS (DBVPG 36P) and deposited at the DBVPG with deposit number 36P, the method comprising:
   inoculating a food with the strain; and
   allowing the food to undergo alcoholic fermentation,
   wherein the food is a grape juice and the alcoholic fermentation is a vinification process that converts the grape juice to a wine, and
   wherein the *Saccharomyces bayanus* subsp. *uvarum* generates more malic acid as compared to a vinification process of the same grape juice using a *Saccharomyces cerevisiae* strain.

2. The method according to claim 1, wherein the strain is in a cream form, desiccated form, lyophilized form, or in the form of a paste when inoculating the food.

3. The method according to claim 1, wherein the grape juice is produced from grapes selected from white berry grapes or red berry grapes.

4. The method according to claim 1, wherein the wine contains glycerol and malic acid naturally produced by the strain in the following concentrations: glycerol higher than about 8.5 g/l; malic acid higher than about 0.5 g/l.

5. The method according to claim 1, wherein the wine contains glycerol higher than about 9.5 g/l and malic acid higher than about 1 g/l.

6. The method according to claim 1, wherein the wine contains glycerol higher than about 10 g/l and malic acid higher than about 2 g/l.

7. The method according to claim 1, wherein the wine contains malic acid at a concentration of about 2 g/l or more.

8. The method according to claim 1, wherein the wine contains malic acid at a concentration of about 2.5 g/l or more.

9. The method according to claim 1, wherein the wine contains malic acid at a concentration of about 3 g/l or more.

10. A method of using a strain of *Saccharomyces bayanus* subsp. *uvarum* identified as SERIUS (DBVPG 36P) and deposited at the DBVPG with deposit number 36, the method comprising:
    producing a dietary supplement or food product containing the strain, wherein the strain itself functions as a probiotic within the dietary supplement or food product independent of other components of the dietary supplement or food product.

11. The method according to claim 10, wherein the food product is formed from a single alcoholic fermentation with the *Saccharomyces bayanus* subsp. *uvarum*.

* * * * *